United States Patent [19]
Asnis et al.

[11] Patent Number: 5,997,538
[45] Date of Patent: Dec. 7, 1999

[54] ROTATIONALLY RATCHETING BONE SCREW

[75] Inventors: Stanley Asnis, Sands Point; Galateia Kazakia; Bruce H. Robie, both of New York, all of N.Y.

[73] Assignee: New York Society for the Ruptured and Crippled Maintaining the Hospital for Special Surgery, New York, N.Y.

[21] Appl. No.: 09/046,458

[22] Filed: Mar. 23, 1998

[51] Int. Cl.⁶ .......................... A61B 17/56; A61B 17/58; A61F 2/30
[52] U.S. Cl. ............................................................. 606/61
[58] Field of Search .......................................... 606/61, 62

[56] References Cited

U.S. PATENT DOCUMENTS

| | | |
|---|---|---|
| 676,678 | 6/1901 | Ellifrits . |
| 829,216 | 8/1906 | Jones . |
| 1,085,041 | 1/1914 | Haughey . |
| 1,547,983 | 7/1925 | Weaver . |
| 5,167,664 | 12/1992 | Hodorek . |
| 5,628,752 | 5/1997 | Asnis et al. . |
| 5,713,708 | 2/1998 | Van DerDrift et al. ................ 411/208 |

Primary Examiner—Michael Buiz
Assistant Examiner—Vy Q. Bui
Attorney, Agent, or Firm—Darby & Darby

[57] ABSTRACT

A rotationally ratcheting bone screw including a body having a distal end formed with an engagement tip for engaging bone tissue, and a shaft formed with a unidirectional stop. The bone screw further includes a fastening element formed with an opening complementally configured to receive the shaft and responsive to relative rotation between the shaft and fastening element to axially advance along the shaft. The fastening element includes a rotationally sensitive ratchet element to cooperate with the stop and inhibit relative counter-rotation between the shaft and the fastening element.

40 Claims, 2 Drawing Sheets

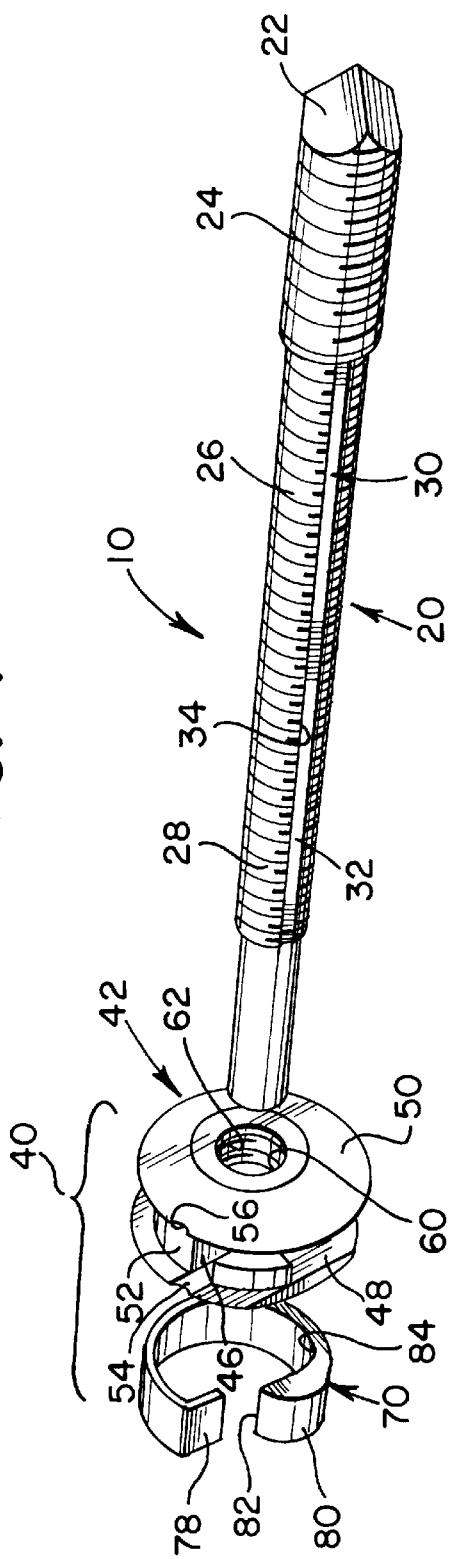
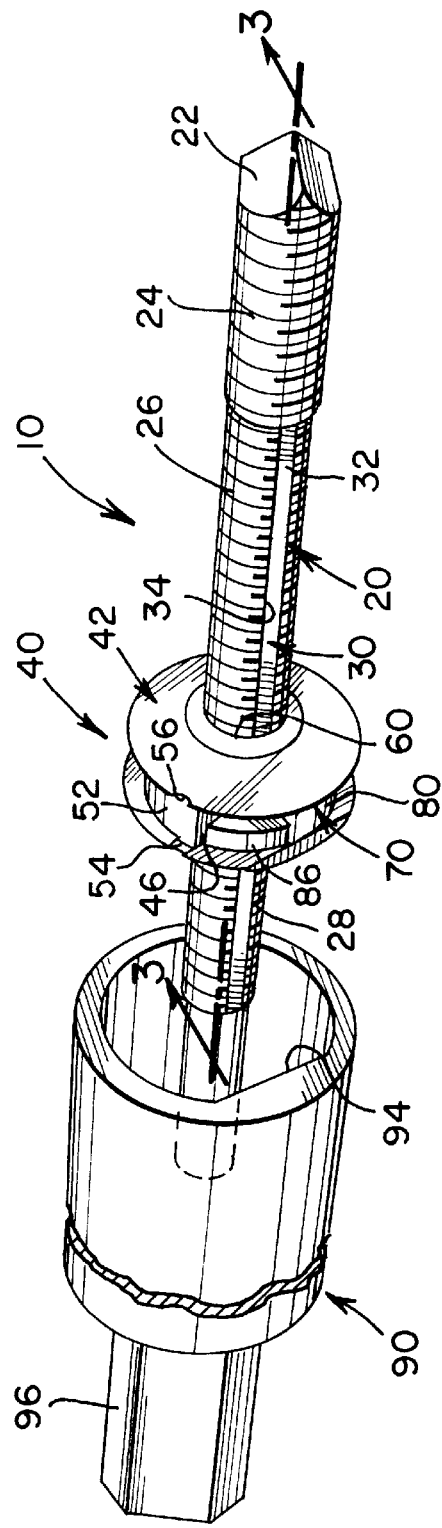

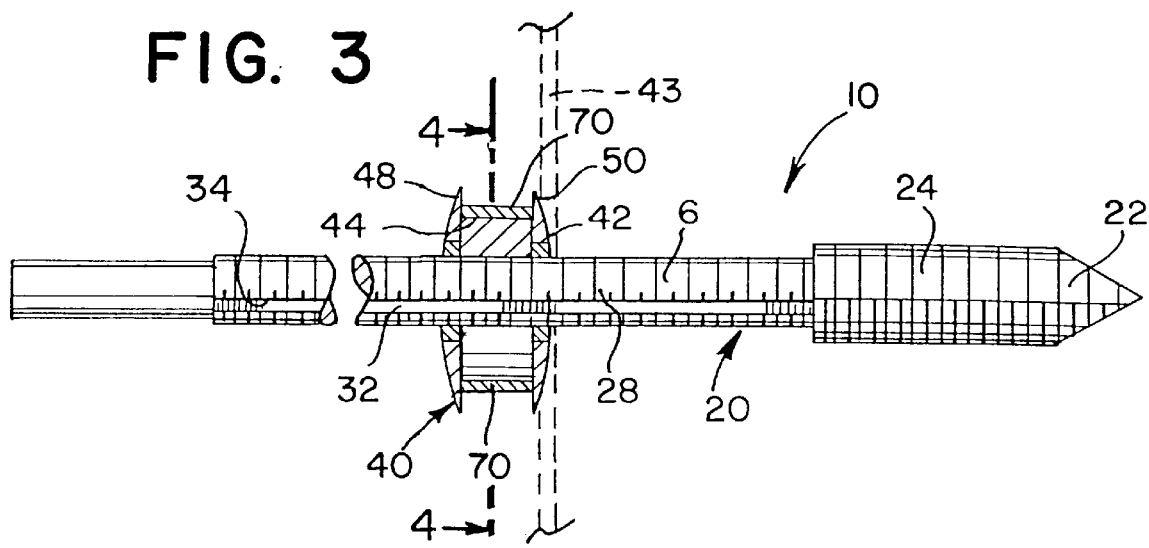
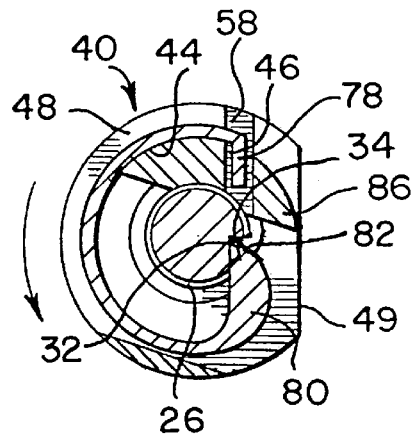
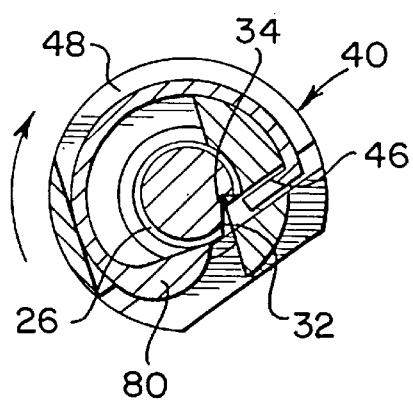
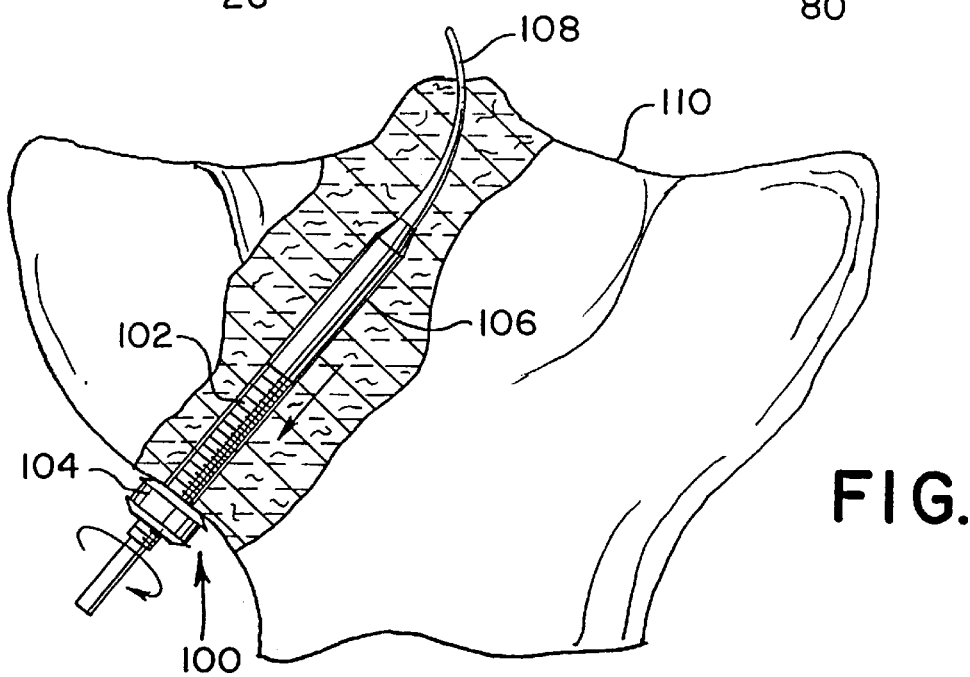

ROTATIONALLY RATCHETING BONE SCREW

FIELD OF THE INVENTION

The invention relates to orthopaedic implants and more particularly an adjustable bone screw having a rotationally ratcheting mechanism for compressing and clamping a patient's bone tissue.

BACKGROUND OF THE INVENTION

Bone screws are utilized in a variety of medical procedures to take advantage of the natural anchoring properties of bone tissue. Such procedures often involve fastening multiple bone fragments of a bone fracture together, or mounting one or more prosthetic elements to the bone in an effort to improve patient mobility. Bone plates are often also utilized in cooperation with a bone screw to provide a more distributed area of compression against the bone being clamped.

The classical bone screw construction comprises an integrally formed fastener having at one end a threaded shaft of a predetermined length to penetrate the bone to a predetermined depth and a fixed radial head formed with a compression flange disposed at the opposite end. In operation, a physician first determines the proper size of bone screw to install from an array of stocked sizes. Once the appropriate size is selected, the screw is implanted into the bone by drilling the threaded end of the bone screw into the bone, for example, across a bone fracture, and utilizing the head as a clamping element.

While the classical bone screw design works well for its intended uses, different orthopedic applications typically require differently sized bone screw shafts or heads in order to adequately anchor or provide proper compression. Consequently, due to the integral nature of the classical bone screw, treatment centers often must stock an assortment of differently sized bone screws in preparation for any type of bone screw application. This tends to create substantial up-front procurement costs to either the supplier or user institution. Moreover, because the classical screw length is fixed, the surgeon must undertake a fairly accurate pre-implant measurement to properly determine the appropriate sized bone screw. Should the measurement prove less than satisfactory, the head may project beyond the expected compression point, requiring removal and replacement of the screw.

In an effort to solve the problems described above, one proposal for a bone screw, disclosed in U.S. Pat. No. 5,628,752 to Asnis et al., implements a two-piece structure including a shaft formed with bone thread at its proximal end and a nut. The shaft is formed with a plurality of axial in-line teeth projecting angularly toward the shaft proximal end. The nut is complementally formed to slide axially along the shaft in the direction of the proximal end and includes an inwardly projecting radial tab or pawl that prevents axial backing-out of the nut by engaging the previously passed tooth. In operation, the screw shaft is drilled into the bone tissue and the nut advanced axially along the shaft until adequate compression between the screw and the nut is obtained. Any excess shaft projecting beyond the nut is typically cut. As a result, the bone screw is adaptable to a variety of bone screw applications due to its variable length.

A second proposal, disclosed in U.S. Pat. No. 5,167,664 to Hodorek, utilizes a similar linear ratcheting feature by including a screw shaft formed with circumferential external teeth. The teeth engage circumferential internal grooves formed within a head to effect unidirectional axial adjustment. Operation of the Hodorek device is similar to that of the Asnis device.

Although the proposals described above work well to minimize the aforementioned problems inherent in a classical type of bone screw, the linear ratcheting feature is incapable of interfacing with conventional surgical power tools. Because of this problem, implanting a bone screw of the linear ratcheting construction often involves more effort and time on the part of the physician. Moreover, non-conventional tooling capable of interfacing with a linear ratcheting bone screw is often substantially more costly than readily available conventional tools.

Thus, the need exists for a bone screw capable of rotationally ratcheting to allow a convenient interface with conventional surgical power tools. The need also exists for a uniform bone screw construction to maximize the reduced costs inherent with wholesale purchasing. The bone screw of the present invention satisfies these needs.

SUMMARY OF THE INVENTION

The present invention provides the capability of rotationally ratcheting an adjustable bone screw head with respect to an anchored shaft to modify the bone screw length and adapt to a variety of bone screw applications. By implementing such a feature, conventional surgical power tools may be employed to aid a physician during the implant procedure. Further, the costs involved in ordering and stocking a variety of differently sized parts are significantly reduced due to the inherent advantages involved in wholesale buying. Moreover, implanting an adjustable bone screw according to the present invention allows adjustment to intraoperative changes and improper pre-operation sizing, substantially reducing the incidence of bone screw removal and replacement.

To realize the advantages above, in one form the invention comprises a rotationally ratcheting bone screw including a body having a distal end formed with an engagement tip for engaging bone tissue, and a shaft formed with a unidirectional stop. The bone screw further includes a fastening element formed with an opening complementally configured to receive the shaft and responsive to relative rotation between the shaft and fastening element to axially advance along the shaft. The fastening element includes a rotationally sensitive ratchet element to cooperate with the stop and inhibit relative counter-rotation between the shaft and the fastening element.

In another form, the invention comprises a rotationally ratcheting bone screw kit comprising a set of disassembled components. The components include a body having a distal end formed with an engagement top for penetrating into bone tissue, and a shaft formed with a unidirectional stop. A fastening element is formed with an opening complementally configured and adapted to receive the shaft when assembled and responsive to relative rotation between the shaft and fastening element to axially advance along the shaft. The fastening element includes a rotationally sensitive ratchet element to cooperate with the stop and inhibit relative counter-rotation between the shaft and the fastening element.

In yet another form, the invention is directed to a rotationally ratcheting bone screw system including a body having a distal end formed with an engagement tip for penetrating into bone tissue, and a shank formed with a unidirectional stop. A fastening element is formed with an opening complementally configured to receive the shaft and responsive to relative rotation between the shaft and fastening element to axially advance along the shaft. The fastening element includes a rotationally sensitive ratchet element to cooperate with the stop and inhibit relative counter-rotation between the shaft and the fastening element. Also included in the system is an elongated tubular installation instrument for percutaneous insertion and torquing of the assembled bone screw and fastening element and having an internal configuration complementally formed to fit around the fastening element to effect torquing thereof.

Other features and advantages of the present invention will be apparent from the following detailed description when read in conjunction with the accompanying drawings.

BRIEF DESCRIPTION OF THE DRAWINGS

FIG. 1 is an exploded perspective view of a bone screw according to one embodiment of the present invention;

FIG. 2 is an exploded perspective view similar to FIG. 1

FIG. 3 is an axial cross-sectional view along line 3—3 of FIG. 2;

FIG. 4 is a radial cross-sectional view along line 4—4 of FIG. 3;

FIG. 5 is a radial cross-sectional view similar to FIG. 4; and

FIG. 6 is a soft tissue tensioner according to a second embodiment of the present invention.

DETAILED DESCRIPTION OF THE INVENTION

Referring now to FIG. 1, the bone screw of the present invention generally designated 10, includes an elongated shaft 20 that cooperates with a fastening element 40 to permit unidirectional rotation while inhibiting relative counter-rotation between the shaft and the fastening element. This construction allows for installation of a predetermined length shaft while allowing a variety of screw lengths.

With reference to FIGS. 1, 2, 3 and 5, the bone screw shaft 20 includes a distal end 22 formed with standard "oversized-in-diameter" right-hand bone threads 24 for penetrating and anchoring into bone tissue. Formed adjacent to the bone thread and extending radially and axially along an intermediate portion 26 of the shaft are external right-hand threads 28 for engaging the fastening element 40. A step-shaped groove 30 is formed axially along the surface of the shaft and includes an oblique flat 32 terminating in a radially directed wall 34 to define a unidirectional radial stop.

Referring to FIGS. 1, 3 and 4, the fastening element 40 includes a multi-piece construction comprising a spool-shaped head 42 and a clip-in ratchet element 70. The head includes a hub 44 (FIG. 3) having a flat portion 46 (FIG. 1) and positioned centrally between respective oppositely disposed flanges 48 and 50 to define a drop-center 52. The respective flanges are formed with inwardly confronting grooves 54 and 56 (FIG. 1) adjacent to and aligned in parallel with the flat portion 46 of the hub to define a slot 58 (FIG. 4). One of the flanges 48 includes a formed peripheral flat 49 to assist in torquing the head. A throughbore 60 is formed centrally through the hub and includes formed right-hand threads 62 configured to threadably receive the intermediately disposed shaft threads 28. A tooth passage (not shown) is formed between the throughbore and the drop-center. In an alternative embodiment, the head 42 is mounted to a bone plate 43 (shown in phantom, FIG. 3) having a bore axially aligned with the head throughbore 60. This is especially useful for plate fixation.

With reference to FIGS. 1 and 4, the ratchet element 70 comprises an integrally formed semi-circular clip configured to complementally nest in the hub drop-center 52. The clip is formed of a resilient material and includes a first end 78 shaped radially inwardly to engage the head slot 58. The second end includes an oversized-in-cross-section tooth 80 having a pointed tip 82 projecting radially inwardly at 84, and in confronting relations to the end 78. The tooth projects through the tooth passage and impinges on the outer radius of the shaft intermediate threads 28. To prevent the clip from flexing beyond a predetermined angle, a support 86 is formed along the interior faces of the flanges 48 and 50.

As an aid in manipulating the fastening element 40 along the shaft 20, an installation instrument is included in a bone screw system of the present invention, generally designated 90, and shown in FIG. 2. The instrument includes a hollow cylindrical socket 92 having a formed flange 94 to complementally engage the head flat 49. A multi-flat fitting 96 projects axially from the socket to permit straightforward torquing of the head.

Manufacture, assembly and packaging of the bone screw 10 of the present invention may be carried out according to acceptable component fabrication practices well known to those skilled in the art. The flexibility in the design of the present invention allows for a variety of packaging schemes to fit the supply needs of the medical industry. For example, the bone screw components may be pre-assembled and packaged together as a unit, or packaged as a kit of unassembled components, or even packaged and sold separately as individual components.

In operation, the bone screw of the present invention adapts to a variety of internal and external fixation applications. Generally, the procedure begins with the physician making necessary incisions to provide adequate access to predetermined bone tissue defining a desired anchoring point. Because of the convenient adjustability of the fastening element 40 with respect to the shaft 20, preliminary measurements and calculations performed by the physician to estimate an exact shaft size for installation are substantially minimized. As a result, the procedure continues by inserting the bone screw 10 through the prepared access area, and drilling the distal threaded end of the shaft into the bone tissue to a predetermined depth with a suitable drill as is well known in the art.

Once the shaft 20 attains the desired depth within the bone tissue, the fastening element 40 is then rotated onto the shaft intermediate threads 28 in a clock-wise manner. Because the tip 82 of the ratchet element 70 rides the shaft radial periphery, each full 360 degree rotation results in an audible "click", signaling engagement of the ratchet tooth 80 with the axial groove 30. The head is rotated and advanced along the shaft until the outboard face of the flange 50 touches the surface of the bone. At this point, the physician continues rotation of the head to the next "click" to position the tooth in engagement with the groove and maintain the bone screw in compression with the bone tissue.

In compression, the fastening element 40 is constantly urged axially toward the proximal end of the shaft 20. With the ratchet element 70 left in engagement with the groove 30, the compression tends to slightly counter-rotate the ratchet element, causing the ratchet top 82 to abut the radially projecting wall 34 of the groove. Once this occurs, the ratchet element is effectively stopped from counter-rotating any further. This effect is translated to the end 78 which exerts an inhibiting force on the head 42 to prevent any further counter-rotation thereof. Once the head is successfully positioned, the excess length of the shaft may be selectively cut and removed, or connected to an external fixator.

Referring now to FIG. 6, a second embodiment of the present invention, generally designated 100, comprises a soft tissue tensioner and includes many of the features of the first embodiment such as a shaft 102 and a fastening element 104. The fastening element construction is identical to that of the first embodiment and warrants no further description. However, the shaft is modified to include an interface 106 for capturing soft tissue, rather than a bone screw thread.

In operation, for example during a procedure to tension an ACL 108 at a tibia 110, the shaft is attached to the distal end of the ACL and then inserted through a drill hole in the tibia. The lower end of the shaft projects through the lateral cortex. The fastening element 104 is then advanced onto the shaft and rotated about the shaft threads until it contacts the cortex. Further rotation of the fastening element draws the shaft axially through the drill hole towards the fastening element, thereby tensioning the ACL. During the process, the shaft, and thus the ACL, is restricted from rotating either by friction against the inner surface of the drill hole, or by manual control. The ratcheting feature of the present invention prevents reverse rotation of the shaft relative to the fastening element which would undesirably cause subsequent loosening of the ACL.

Those skilled in the art will appreciate the many benefits and advantages of the present invention. Of significant importance is the rotationally ratcheting feature of the present invention that allows a uniformly sized bone screw or soft tissue tensioner shaft to adapt and adjust to a variety of dimensional treatment situations. This feature reduces inventory costs by reducing the number of bone screw lengths. Moreover, because of its rotational nature, the present invention is particularly suited for interfacing with convenient surgical power tools. This minimizes the effort, time and costs experienced by physicians in implanting bone screws.

While the invention has been particularly shown and described with reference to the preferred embodiments thereof, it will be understood by those skilled in the art that various changes in form and detail may be made therein without departing from the spirit and scope of the invention. For example, while a significant portion of the foregoing disclosure relates to the field of bone screws, it is to be understood that the rotationally ratcheting construction may be extended to any fastening application.

What is claimed is:

1. A rotationally ratcheting bone screw comprising:
    a body having a distal end with an engagement tip for engaging bone tissue, and a shaft having a unidirectional stop and threads defined therein; and
    a fastening element with an opening complementary configured to receive said shaft, said fastening element including a head having an outer surface, and a rotationally sensitive ratchet element cooperating with said stop and inhibiting relative counter-rotation between said shaft and said fastening element, said ratchet element being disposed about at least a portion of the outer surface of said head, said fastening element and said body being operative in response to relative rotation therebetween to effect relative axial displacement.

2. A rotationally ratcheting bone screw according to claim 1, wherein said head is coaxially disposed on said shaft so as to be rotationally adjustable thereon.

3. A rotationally ratcheting bone screw according to claim 1, further comprising a plate, said head being disposed on said plate and receiving said shaft.

4. A rotationally ratcheting bone screw according to claim 1, wherein said engagement tip is formed with a standard bone thread.

5. A rotationally ratcheting bone screw according to claim 1, wherein said engagement tip is formed with a soft tissue interface.

6. A rotationally ratcheting bone screw according to claim 1, wherein said shaft is formed with external threads and said head is formed with internal threads to threadably engage said shaft and effect axial movement of said head along said shaft in response to relative rotational movement between said head and shaft.

7. A rotationally ratcheting bone screw according to claim 1, wherein said shaft has an outwardly opening axial groove defined therein to form said unidirectional stop.

8. A rotationally ratcheting bone screw according to claim 7, wherein said groove has a depth no greater than a depth of said shaft threads.

9. A rotationally ratcheting bone screw according to claim 8, wherein said fastening element includes a ratchet tooth to engage said groove when said fastening element is counter-rotated.

10. A rotationally ratcheting bone screw according to claim 1, wherein said head is spool-shaped with an annular drop-center portion, and said ratchet element is adapted to nest in said drop-center and has a ratchet tooth projecting radially inward.

11. A rotationally ratcheting bone screw according to claim 10, wherein said drop-center portion has an axial slot defined therein, and said ratchet element includes a mounting tab to complementally engage said slot and couple said ratchet element to said head.

12. A rotationally ratcheting bone screw according to claim 10, wherein said head has a support wall overlying a portion of said drop-center proximate said ratchet tooth.

13. A rotationally ratcheting bone screw for placing bone tissue in compression, said bone screw comprising:
    a body having a distal end with bone threads for engaging bone tissue, and a shaft having external intermediate threads and an outwardly opening axial groove defining a unidirectional stop; and
    a fastening element including a spool-shaped head having an opening complementally configured to receive said shaft and having an annular drop-center portion, said fastening element further including a ratchet element having a ratchet tooth, said ratchet element being adapted to nest in said drop-center to engage said groove when said fastening element is counter-rotated.

14. A rotationally ratcheting soft tissue tensioner for attaching to soft tissue and placing said soft tissue in tension, said soft tissue tensioner comprises:
    a body having a distal end with a soft tissue interface for attaching to said soft tissue, and a shaft having external intermediate threads and an outwardly opening axial groove defining a unidirectional stop; and
    a fastening element including a spool-shaped head with an opening complementally configured to receive said shaft and an annular drop-center portion, said fastening element further including a ratchet element having a ratchet tooth, said ratchet element being adapted to nest in said drop-center to engage said groove when said fastening element is counter-rotated.

15. A rotationally ratcheting bone screw kit comprising a set of disassembled components, said components comprising:
    a body having a distal end with an engagement tip for engaging bone tissue, and a shaft having a unidirectional stop; and a fastening element with an opening complementally configured and adapted to receive said shaft when assembled, said fastening element including a head having an outer surface, and a rotationally sensitive ratchet element to cooperate with said stop and inhibit relative counter-rotation between said shaft and said fastening element, said ratchet being disposed about at least a portion of the outer surface of said head, said fastening element and said body being operative in response to relative rotation therebetween to effect relative axial displacement.

16. A rotationally ratcheting bone screw kit according to claim 15, further comprising an elongated tubular installation instrument for percutaneous insertion and torquing of at least one of said assembled bone screw and said fastening element, and having an internal configuration complementally formed to fit around said fastening element to effect torquing thereof.

17. A rotationally ratcheting bone screw system comprising:
   a body having a distal end with an engagement tip for engaging bone tissue, and a shaft having a unidirectional stop;
   a fastening element with an opening complementally configured to receive said shaft, said fastening element including a head having an outer surface, and a rotationally sensitive ratchet element to cooperate with said stop and inhibit relative counter-rotation between said shaft and said fastening element, said ratchet being disposed about at least a portion of the outer surface of said head, said fastening element and said body being operative in response to relative rotation therebetween to effect relative axial displacement; and
   an elongated tubular installation instrument for percutaneous insertion and torquing of at least one of said assembled bone screw and said fastening element, and having an internal configuration complementally formed to fit around said fastening element to effect torquing thereof.

18. A method of implanting a bone screw including an elongated body with a distal tip, threads and a unidirectional stop and, said bone screw further including a fastening element with a threaded opening defined therein so as to be threadably coupled to said shaft, said fastening element including a head having an outer surface and a rotationally sensitive ratchet element disposed about at least a portion of the outer surface of said head for engaging said stop, said method comprising the steps of:
   drilling said distal tip into a predetermined section of bone tissue to a predetermined depth;
   rotating said fastening element about said body to incrementally advance said element axially along said shaft and periodically bring said ratchet element and said stop into engagement; and
   tightening said fastening element against said bone tissue to generate compression while bringing said ratchet element and stop into engagement to inhibit counter-rotation and maintain said compression on said bone tissue.

19. A method of attaching soft tissue to bone tissue, said method comprising the steps of:
   drilling an attachment passage through said bone tissue;
   selecting a soft tissue tensioner including an elongated body formed with a distal tip having a soft tissue interface, threads and a unidirectional stop, said soft tissue tensioner further including a fastening element with a threaded opening so as to be threadably coupled to said shaft, said fastening element including a head having an outer surface and a rotationally sensitive ratchet element disposed about at least a portion of the outer surface of said head for engaging said stop;
   inserting said soft tissue tensioner through said passage to position said interface proximate said soft tissue;
   capturing said soft tissue with said soft tissue interface;
   rotating said fastening element about said body to abut said bone tissue and incrementally draw said shaft axially through said passage to place said soft tissue in tension; and
   bringing said ratchet element and said stop into fixed engagement to maintain said tension on said soft tissue.

20. A rotationally ratcheting fastener comprising:
   a body including a threaded shaft with a distal engagement tip, said body having a longitudinal groove extending axially to define a unidirectional stop;
   a spool-shaped head with a central threaded throughbore for coupling to said threaded shaft, said head including respective oppositely disposed flanges defining a drop-center and a tooth passage extending from said drop-center to said throughbore; and
   a ratchet element disposed annularly in said drop-center and including a tooth capable of projecting through said tooth passage and engaging said unidirectional stop to inhibit relative rotation in a preselected direction.

21. A rotationally ratcheting tensioning device comprising:
   a body including a threaded shaft with a distal interface to capture material to be tensioned, said body having a longitudinal groove extending axially to define a unidirectional stop;
   a spool-shaped head with a central threaded throughbore for coupling to said threaded shaft, said head including respective oppositely disposed flanges defining a drop-center and a tooth passage extending from said drop-center to said throughbore; and
   a ratchet element disposed annularly in said drop-center and including a tooth capable of projecting through said tooth passage and engaging said unidirectional stop to inhibit rotation in a preselected direction.

22. A rotationally ratcheting bone screw for placing bone tissue in compression, said bone screw comprising:
   a body having a distal end with bone threads for engaging bone tissue, and a shaft having threads and an outwardly opening axial groove defining a unidirectional stop; and
   a fastening element including a spool-shaped head having an opening complementally configured to receive said shaft and having an annular drop-center portion, said fastening element further including a ratchet element having a ratchet tooth, said ratchet element being adapted to nest in said drop-center to engage said groove when said fastening element is counter-rotated.

23. A rotationally ratcheting soft tissue tensioner for attaching to soft tissue and placing said soft tissue in tension, said soft tension tensioner comprising:
   a body having a distal end with a soft tissue interface for attaching to said soft tissue, and a shaft having threads and an outwardly opening axial groove defining a unidirectional stop; and
   a fastening element including a spool-shaped head with an opening complementally configured to received said shaft therein and an annular drop-center portion, said fastening element further including a ratchet element having a ratchet tooth, said ratchet element being adapted to nest in said drop-center to engage said groove when said fastening element is counter-rotated.

24. A rotationally ratcheting bone screw comprising:
a body having a distal end with an engagement tip for engaging bone tissue, and a shaft having a unidirectional stop and threads defined therein; and
a fastening element with an opening complementary configured to receive said shaft, said fastening element including a head disposed about said shaft and a rotationally sensitive ratchet element substantially disposed circumferentially about said shaft to cooperate with said stop and inhibit relative counter-rotation between said shaft and said fastening element, said ratchet element being substantially constrained from rotating relative to said head, said fastening element and said body being operative in response to relative rotation therebetween to effect relative axial displacement.

25. A rotationally ratcheting bone screw according to claim 24, wherein said head is coaxially disposed on said shaft so as to be rotationally adjustable thereon.

26. A rotationally ratcheting bone screw according to claim 24, further comprising a plate, said head being disposed on said plate for receiving said shaft.

27. A rotationally ratcheting bone screw according to claim 24, wherein said engagement tip is formed with a standard bone thread.

28. A rotationally ratcheting bone screw according to claim 24, wherein said engagement tip is formed with a soft tissue interface.

29. A rotationally ratcheting bone screw according to claim 24, wherein said shaft is formed with external threads and said head is formed with internal threads to threadably engage said shaft and effect axial movement of said head along said shaft in response to relative rotational movement between said head and shaft.

30. A rotationally ratcheting bone screw according to claim 24, wherein said shaft has an outwardly opening axial groove defined therein to form said unidirectional stop.

31. A rotationally ratcheting bone screw according to claim 30, wherein said groove has a depth no greater than a depth of said shaft threads.

32. A rotationally ratcheting bone screw according to claim 31, wherein said fastening element includes a ratchet tooth to engage said groove when said fastening element is counter-rotated.

33. A rotationally ratcheting bone screw according to claim 24, wherein said head is spool-shaped with an annular drop-center portion, and said ratchet element is adapted to nest in said drop-center and has a ratchet tooth projecting radially inward.

34. A rotationally ratcheting bone screw according to claim 33, wherein said drop-center portion has an axial soft defined therein, and said ratchet element includes a mounting tab to complementally engage said slot and couple said ratchet element to said head.

35. A rotationally ratcheting bone screw according to claim 33, wherein said head has a support wall overlying a portion of said drop-center proximate said ratchet tooth.

36. A rotationally ratcheting bone screw kit comprising a set of disassembled components, said components comprising:
a body having a distal end with an engagement tip for engaging bone tissue, and a shaft having a unidirectional stop; and a fastening element with an opening complementally configured and adapted to receive said shaft when assembled, said fastening element including a head disposed about said shaft and a rotationally sensitive ratchet element substantially disposed circumferentially about said shaft to cooperate with said stop and inhibit relative counter-rotation between said shaft and said fastening element, said ratchet element being substantially constrained from rotating relative to said head, said ratchet element and said body being operative in response to relative rotation therebetween to effect relative axial displacement.

37. A rotationally ratcheting bone screw kit according to claim 36, further comprising an elongated tubular installation instrument for percutaneous insertion and torquing of at least one of said assembled bone screw and said fastening element, and having an internal configuration complementally formed to fit around said fastening element to effect torquing thereof.

38. A rotationally ratcheting bone screw system comprising:
a body having a distal end with an engagement tip for engaging bone tissue, and a shaft having a unidirectional stop;
a fastening element with an opening complementally configured to receive said shaft, said fastening element including a head disposed about said shaft and a rotationally sensitive ratchet element substantially disposed circumferentially about said shaft to cooperate with said stop and inhibit relative counter-rotation between said shaft and said fastening element, said ratchet element being substantially constrained from rotating relative to said head, said fastening element and said body being operative in response to relative rotation therebetween to effect relative axial displacement; and
an elongated tubular installation instrument for percutaneous insertion and torquing of at least one of said assembled bone screw and said fastening element, and having an internal configuration complementally formed to fit around said fastening element to effect torquing thereof.

39. A method of implanting a bone screw including an elongated body with a distal tip, threads, and a unidirectional stop, said bone screw further including a fastening element with a threaded opening defined therein so as to be threadably coupled to said shaft, said fastening element including a head disposed about said shaft and a rotationally sensitive ratchet element substantially disposed circumferentially about said shaft for engaging said stop, said method comprising the steps of:
drilling said distal tip into a predetermined section of bone tissue to a predetermined depth;
rotating said fastening element about said body to incrementally advance said element axially along said shaft and periodically bring said ratchet element and said stop into engagement; and
tightening said fastening element against said bone tissue to generate compression while bringing said ratchet element and stop into engagement to inhibit counter-rotation and maintain said compression on said bone tissue, said ratchet element being substantially constrained from rotating relative to said head.

40. A method of attaching soft tissue to bone tissue, said method comprising the steps of:
drilling an attachment passage through said bone tissue;

selecting a soft tissue tensioner including an elongated body formed with a distal tip having a soft tissue interface with threads and a unidirectional stop, said soft tissue tensioner further including a fastening element with a threaded opening so as to be threadably coupled to a shaft, said fastening element including a head disposed about said shaft and a rotationally sensitive ratchet element substantially disposed circumferentially about said shaft for engaging said stop;

inserting said soft tissue tensioner through said passage to position said interface proximate said soft tissue;

capturing said soft tissue with said soft tissue interface;

rotating said fastening element about said body to abut said bone tissue and incrementally draw said shaft axially through said passage to place said soft tissue in tension, said ratchet element being substantially constrained from rotating relative to said head; and bringing said ratchet element and said stop into fixed engagement to maintain said tension on said soft tissue.

* * * * *